United States Patent
Barone et al.

(10) Patent No.: US 11,918,761 B2
(45) Date of Patent: Mar. 5, 2024

(54) INTRAVASCULAR IMAGING CATHETER SYSTEM WITH FORCE ERROR DETECTION AND AUTOMATIC REMEDIATION VIA PULLBACK AND ROTATION FOR TRANSLATING AND ROTATING A TORQUE CABLE IN A CATHETER

(71) Applicant: Infraredx, Inc., Burlington, MA (US)

(72) Inventors: David Barone, Lexington, MA (US); Todd Bitner, Waltham, MA (US); John N. Beck, Hopkinton, MA (US)

(73) Assignee: INFRAREDX, INC., Burlington, MA (US)

( * ) Notice: Subject to any disclaimer, the term of this patent is extended or adjusted under 35 U.S.C. 154(b) by 698 days.

(21) Appl. No.: 16/131,603

(22) Filed: Sep. 14, 2018

(65) Prior Publication Data
US 2020/0086086 A1    Mar. 19, 2020

(51) Int. Cl.
*A61M 25/01* (2006.01)
*A61B 5/00* (2006.01)
(Continued)

(52) U.S. Cl.
CPC ....... *A61M 25/0113* (2013.01); *A61B 5/0075* (2013.01); *A61B 5/0084* (2013.01);
(Continued)

(58) Field of Classification Search
CPC .......... A61M 25/0113; A61M 25/0662; A61M 2205/332; A61M 25/01; A61M 25/06; A61B 8/12; A61B 5/0084; A61B 5/0075; A61B 8/445; A61B 2562/0247; A61B 5/0086; A61B 5/6852; A61B 5/02007; A61B 8/00; A61B 5/00
See application file for complete search history.

(56) References Cited

U.S. PATENT DOCUMENTS 6,949,072 B2    9/2005 Furnish
8,052,605 B2    11/2011 Muller et al.
(Continued)

FOREIGN PATENT DOCUMENTS

WO    2009092059 A1    7/2009

OTHER PUBLICATIONS

Notification of Transmittal of International Search Report and Written Opinion including International Search Report and Written Opinion for International application No. PCT/US18/51121 dated Dec. 4, 2018, 11 pages.
(Continued)

*Primary Examiner* — Serkan Akar
(74) *Attorney, Agent, or Firm* — Jason M. Shapiro; Devlin Law Firm LLC

(57) ABSTRACT

An intravascular imaging system includes a catheter with an elongate outer sheath and a torque cable axially translatable and rotatable in the elongate outer sheath, a pullback and rotation unit for axially translating and rotating the torque cable, a sensor configured to provide an output indicative of an axial force exerted by the torque cable on a rotor in the pullback and rotation unit, and a controller configured to cause the pullback and rotation unit to operate in a remedial mode if the output exceeds a predetermined threshold.

16 Claims, 9 Drawing Sheets

(51) Int. Cl.
*A61B 8/00* (2006.01)
*A61B 8/12* (2006.01)
*A61M 25/06* (2006.01)

(52) U.S. Cl.
CPC ............... *A61B 8/12* (2013.01); *A61B 8/445* (2013.01); *A61M 25/0662* (2013.01); *A61M 2205/332* (2013.01)

(56) References Cited

U.S. PATENT DOCUMENTS

| | | | |
|---|---|---|---|
| 8,157,741 | B2 | 4/2012 | Hirota |
| 2005/0049574 | A1 | 3/2005 | Petrick et al. |
| 2007/0197939 | A1* | 8/2007 | Wallace ................ A61M 25/01 600/587 |
| 2008/0045892 | A1* | 2/2008 | Ferry ................ A61M 25/0113 604/95.01 |
| 2008/0097158 | A1 | 4/2008 | Abele et al. |
| 2008/0097223 | A1 | 4/2008 | Strickler et al. |
| 2008/0097224 | A1 | 4/2008 | Murphy et al. |
| 2008/0097408 | A1 | 4/2008 | Murphy et al. |
| 2009/0281430 | A1 | 11/2009 | Wilder |
| 2012/0071752 | A1* | 3/2012 | Sewell ................ A61B 34/74 600/424 |
| 2014/0277005 | A1* | 9/2014 | Guggenheimer ............................ A61B 17/320783 606/159 |
| 2015/0297864 | A1 | 10/2015 | Kokish et al. |

OTHER PUBLICATIONS

Extended European Search Report in counterpart European Application No. 18933250.5, dated Jun. 4, 2021, 9 pages.
International Preliminary Report on Patentability received in international application No. PCT/US2018/051121, dated Mar. 25, 2021 (10 pages).

* cited by examiner

INTRAVASCULAR IMAGING CATHETER SYSTEM WITH FORCE ERROR DETECTION AND AUTOMATIC REMEDIATION VIA PULLBACK AND ROTATION FOR TRANSLATING AND ROTATING A TORQUE CABLE IN A CATHETER

FIELD OF THE INVENTION

The present invention relates generally to catheters with movable cores and, more particularly, to systems and methods for detecting and remediating force error conditions in such catheters.

BACKGROUND

Catheters with imaging components are commonly used to inspect vessels in the body. Such catheters may include a hollow, tubular sheath made of a flexible material. The sheath may be placed in a vessel using a guidewire and used as a conduit for positioning imaging components in the vessel. For example, imaging components may be mounted at the distal end of a torque cable and advanced into the vessel via the sheath. Depending on the type of information desired, the imaging components may include optical elements such as mirrors or lenses for transmitting and receiving light energy (e.g., near infrared light) and/or transducers for transmitting and receiving sound energy (e.g., ultrasonic pulses). Imaging components may be mounted on an imaging tip at the distal end of a torque cable, and the torque cable may be moved relative to the sheath to obtain information about the vessel. In one example, the imaging tip may be advanced distally to a desired position in the sheath (e.g., a start position) and may then be retracted proximally and rotated to obtain a 360 degree view along a desired portion of the vessel.

The imaging tip at the distal end of the torque cable must be long enough to accommodate one or more imaging sensors and is typically much more rigid than the outer sheath. Thus, if the imaging tip is advanced distally into a portion of the outer sheath that is kinked or tightly curved, there is a possibility of the imaging tip not being able to traverse the outer sheath. In extreme cases, there is also a possibility of the imaging tip damaging the outer sheath or even penetrating though the outer sheath and creating a risk of injury.

SUMMARY OF THE INVENTION

In a first aspect of the invention, a pullback and rotation unit with force error detection and remediation is provided for axially translating and rotating a torque cable in an elongate outer sheath of a catheter. The pullback and rotation unit includes a housing having a longitudinal axis, and a rotor that is disposed in the housing and mounted to be rotatable and linearly translatable relative to the longitudinal axis of the housing. The rotor is further configured to be coupled with a proximal end of the torque cable. The pullback and rotation unit may also include at least one sensor configured to provide an output indicative of an axial force exerted by the torque cable on the rotor in the pullback and rotation unit. The pullback and rotation unit may also include a controller configured to cause the pullback and rotation unit to operate in a remedial mode if the output exceeds a predetermined threshold. The pullback and rotation unit may alleviate problems associated with kinking of an outer sheath in an imaging catheter system and other force error conditions preventing or inhibiting distal translation of the torque cable in the outer sheath.

In an embodiment, the at least one sensor may be mounted on the rotor in the pullback and rotation unit. For example, the at least one sensor may be mounted between a coupling on the rotor configured to couple with the proximal end of the torque cable and a main body of the rotor. These embodiments may improve sensitivity by reducing intervening components between the sensor(s) and the torque cable.

In an embodiment, the coupling may be mounted to move longitudinally relative to the main body of the rotor. This embodiment may facilitate transfer of forces from the coupling to the sensor(s) as opposed to the main body of the rotor.

In an embodiment, the sensor(s) may be mounted on the main body of the rotor. This embodiment may reduce manufacturing costs by allowing the sensor(s) to be positioned near electrical connections in the main body of the rotor.

In an embodiment, the system includes a plurality of sensors, which may improve reliability. The plurality of sensors may be radially spaced from an axis of rotation of the rotor, which may improve the ability of the sensors to detect forces applied to the coupling, particularly when the coupling is mounted to float longitudinally relative to the main body of the rotor.

In an embodiment, the output is an average of the outputs from one or more sensors over a period of time, which can improve reliability of the system and help reduce false alarms. The period of time may be at least one full rotation to further improve reliability.

In an embodiment, the predetermined threshold may correspond to a force greater than an average axial force applied to the coupling during normal operation of the catheter. This embodiment may improve reliability and reduce the occurrence of false alarms. The predetermined threshold may also be set below a level at which damage to the catheter components, such as the outer sheath or the imaging tip, may occur, thereby increasing the possibility that the procedure may be resumed after the error condition is addressed.

In an embodiment, the controller may be configured to cause the rotor, in the remedial mode, to retract proximally a predetermined distance. This embodiment may relieve at least a portion of the axial force applied to the rotor by the torque cable, reducing the possibility of damaging the system and possibly allowing the procedure to be resumed. The controller may be configured to cause the rotor, in the remedial mode, to continue rotating as it is retracted, which can prevent binding of the torque cable in the outer sheath under certain circumstances.

In a second aspect of the invention, an intravascular imaging catheter system includes a pullback and rotation unit according to the first aspect of the invention, and an imaging catheter including an elongate outer sheath having a proximal end coupled with the housing, a torque cable disposed in the outer sheath and having a proximal end coupled with the rotor, and an imaging tip located at a distal end of the torque cable. This aspect may alleviate problems associated with kinking of an outer sheath in an intravascular imaging catheter system and other error conditions preventing or inhibiting distal translation of the torque cable in the outer sheath.

In a third aspect of the invention, a method of imaging a vessel is provided using a catheter including an elongate outer sheath, a torque cable disposed in the outer sheath, and an imaging tip located at a distal end of the torque cable, wherein the imaging tip includes at least one imaging component selected from the group comprising an optical element and an ultrasonic transducer. The method includes the steps of coupling a proximal end of the elongate outer sheath with a housing of a pullback and rotation unit, coupling a proximal end of the torque cable with a rotor disposed within the housing of the pullback and rotation unit, inserting the catheter into a vessel, linearly translating the imaging tip distally relative to the outer sheath by linearly translating the rotor distally in the housing of the pullback and rotation unit, receiving an output from a sensor indicative of an axial force applied to the rotor by the torque cable, and causing the rotor to operate in a remedial mode if the output from the at least one sensor exceeds a predetermined threshold. The method may alleviate problems associated with kinking of an outer sheath in an imaging catheter system and other error conditions preventing or inhibiting distal translation of the torque cable in the outer sheath.

In an embodiment, the at least one sensor may be mounted on a rotor in the pullback and rotation unit. This embodiment may reduce cost by implementing force detection and remediation in a portion of the system that is normally re-used. This arrangement may also facilitate compatibility with existing catheters.

In an embodiment, the at least one sensor may be mounted between a coupling on the rotor configured to couple with the proximal end of the torque cable and a main body of the rotor. This embodiment may improve sensitivity by reducing intervening components between the sensor(s) and the torque cable.

In an embodiment, the coupling may be mounted to move longitudinally relative to the main body of the rotor. This embodiment may facilitate transfer of forces from the coupling to the sensor(s) as opposed to the main body of the rotor.

In an embodiment, the sensor(s) may be mounted on the main body of the rotor. This embodiment may reduce manufacturing costs by allowing the sensor(s) to be positioned near electrical connections.

In an embodiment, the system includes a plurality of sensors, which may improve reliability. The plurality of sensors may be radially spaced from an axis of rotation of the rotor, which may improve the ability of the sensors to detect forces applied to the coupling, particularly when the coupling is mounted to float longitudinally relative to the main body of the rotor.

In an embodiment, the output is an average of the outputs from one or more sensors over a period of time, which can improve reliability of the system and help reduce false alarms. The period of time may be at least one full rotation to further improve reliability.

In an embodiment, the predetermined threshold may correspond to a force greater than an average axial force applied to the coupling during normal operation of the catheter. This embodiment may improve reliability and reduce the occurrence of false alarms. The predetermined threshold may also be set below a level at which damage to the catheter components, such as the outer sheath or the imaging tip, may occur, thereby increasing the possibility that the procedure may be resumed after the error condition is addressed.

In an embodiment, the method may cause the rotor, in the remedial mode, to retract proximally a predetermined distance. This embodiment may relieve at least a portion of the axial force applied to the rotor by the torque cable, reducing the possibility of damaging the system and possibly allowing the procedure to be resumed. The method may also cause the rotor, in the remedial mode, to continue rotating as it is retracted, which can prevent binding of the torque cable in the outer sheath under certain circumstances.

BRIEF DESCRIPTION OF THE DRAWINGS

Embodiments of the invention will be described with reference to the following figures, wherein identical structures, elements or parts which appear in more than one figure are labeled with the same reference number, and in which.

DETAILED DESCRIPTION

Figure 1:
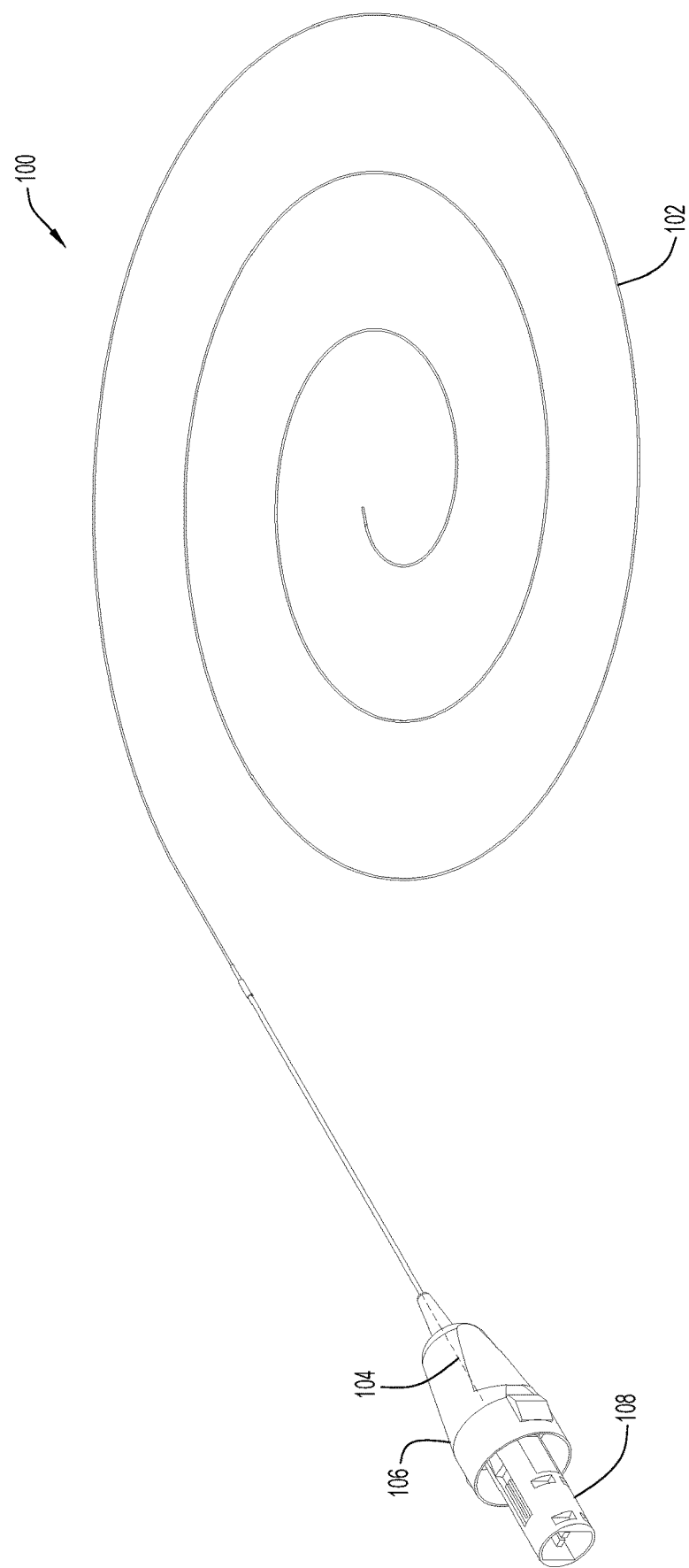
FIG. 1 is a perspective view of an imaging catheter for an imaging catheter system according to an example embodiment of the present invention.

FIG. 1 is a perspective view of an imaging catheter 100 for an imaging catheter system with force error detection and remediation according to an example embodiment. Imaging catheter 100 includes an elongate tubular outer member or sheath 102 configured for insertion into the lumen of a vessel (e.g., using a guidewire), an elongate inner core in the form of a torque cable 104 configured to extend longitudinally within the outer sheath, and outer and inner hubs 106 and 108 at proximal ends of the outer sheath 102 and the torque cable 104, respectively. In the example shown in FIG. 1, the outer hub 106 is hollow, and the inner hub 108 is disposed at least partly within the outer hub and configured to be rotatable and linearly translatable relative to a longitudinal axis of the outer hub. The torque cable 104 extends distally from the inner hub 108 into the outer sheath 102.

In an example embodiment, the outer sheath 102 is composed of a flexible material that is efficiently transmissive (i.e., transparent or translucent) to near infrared light to facilitate use of the imaging catheter for near infrared spectroscopy (NIRS). Such material may be, for example, petrothene or any suitable polymer that efficiently transmits near infrared light. Inside the outer sheath 102 there may be a transmission medium, such as saline or other fluid, to facilitate use of the imaging catheter for intravascular ultrasound (IVUS) imaging. If the transmission medium is also transparent to near infrared light, the imaging catheter may be used for both IVUS and NIRS imaging. Because the outer sheath 102 is composed of a flexible material, it may conform to the shape of the vessel into which it is inserted.

In an example embodiment, the torque cable 104 is constructed using one or more hollow coils of wire composed of a material, such as steel or titanium, capable of transmitting axial forces and torque along the length of the torque cable. Thus, the torque cable 104 may be linearly translated and rotated relative to the longitudinal axis of the outer sheath 102 via linear translation and rotation of the inner hub 108. Due to the coiled structure, the torque cable 104 may also bend somewhat to conform to the shape of the outer sheath 102 inside a vessel. However, if the outer sheath 102 is kinked or positioned in a highly tortuous section of a vessel with tight bends, the torque cable 104 may not be capable of traversing the outer sheath, and a force may be applied by the torque cable against the inner wall of the outer sheath as the torque cable is advanced distally into such a kink or bend. The force applied by the torque cable 104 against the outer sheath 102 may cause damage to the outer sheath or components mounted on the torque cable. At the same time, an axial compression of the torque cable 104 may occur. While a torque cable constructed of one or more hollow coils of wire has been described, it will be appreciated that other types of torque cables can be used, including, but not limited to, thin-walled tubes, spiral-cut tubes, tubes with cutouts to increase flexibility, and other elongate tubular members capable of transmitting torque and being linearly translated through an outer sheath.

Figure 2:
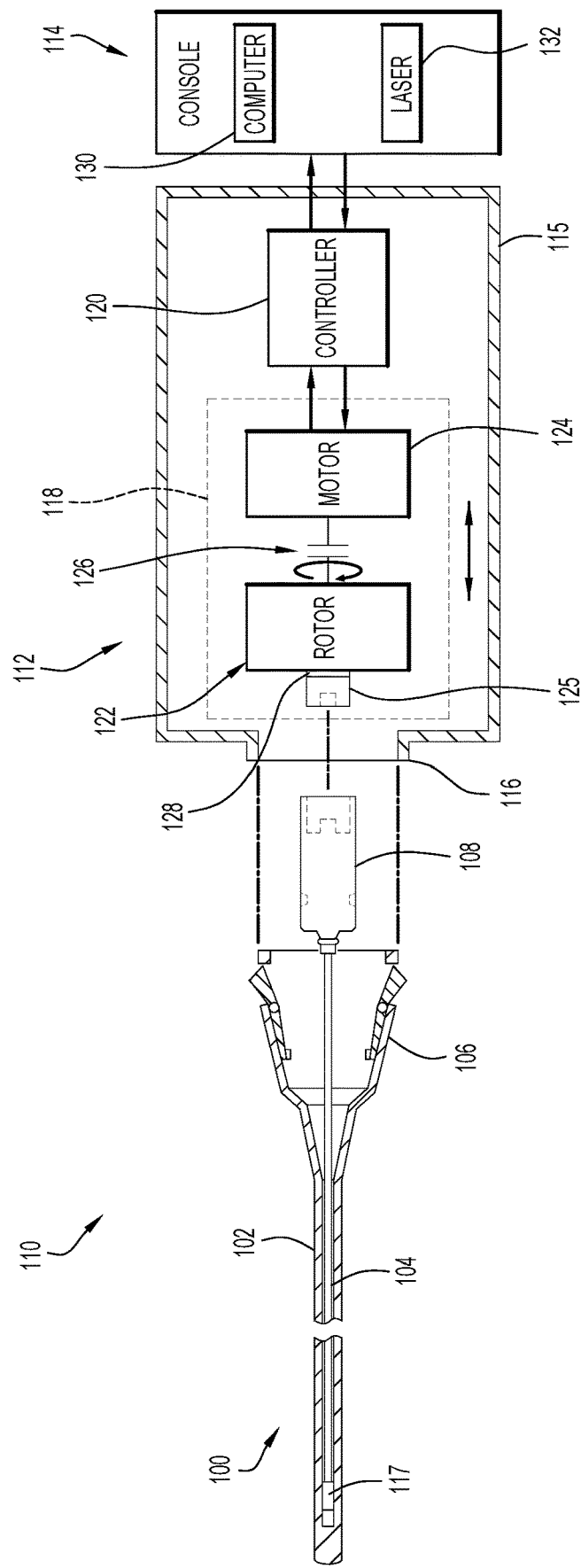
FIG. 2 is an exploded view of an imaging catheter system including an imaging catheter, a pullback and rotation unit, and a console according to an example embodiment of the present invention.

FIG. 2 is an exploded view of an example imaging catheter system 110 capable of detecting kinking and other problems with the catheter 100 based on axial compression of the torque cable 104 and taking remedial actions to prevent damage to the outer sheath 102 or other components of the catheter or the system. The imaging catheter system 110 includes an imaging catheter 100 as described above, a pullback and rotation unit (PBR) 112, and a console 114. The PBR 112 includes a housing 115 with a distal opening 116, a rotor carriage 118 movable linearly along a longitudinal axis of the housing, and a controller 120 for controlling operation of the rotor carriage and communicating with the console 114. Longitudinal travel of the rotor carriage 118 may be effected in a conventional manner, e.g., by means of a lead screw and rotary motor that powers the lead screw via a pulley and belt arrangement. The controller 120 may implemented in hardware (e.g., a circuit, an application specific integrated circuit, a field programmable gate array, etc.), software, or a combination thereof.

Figure 3:
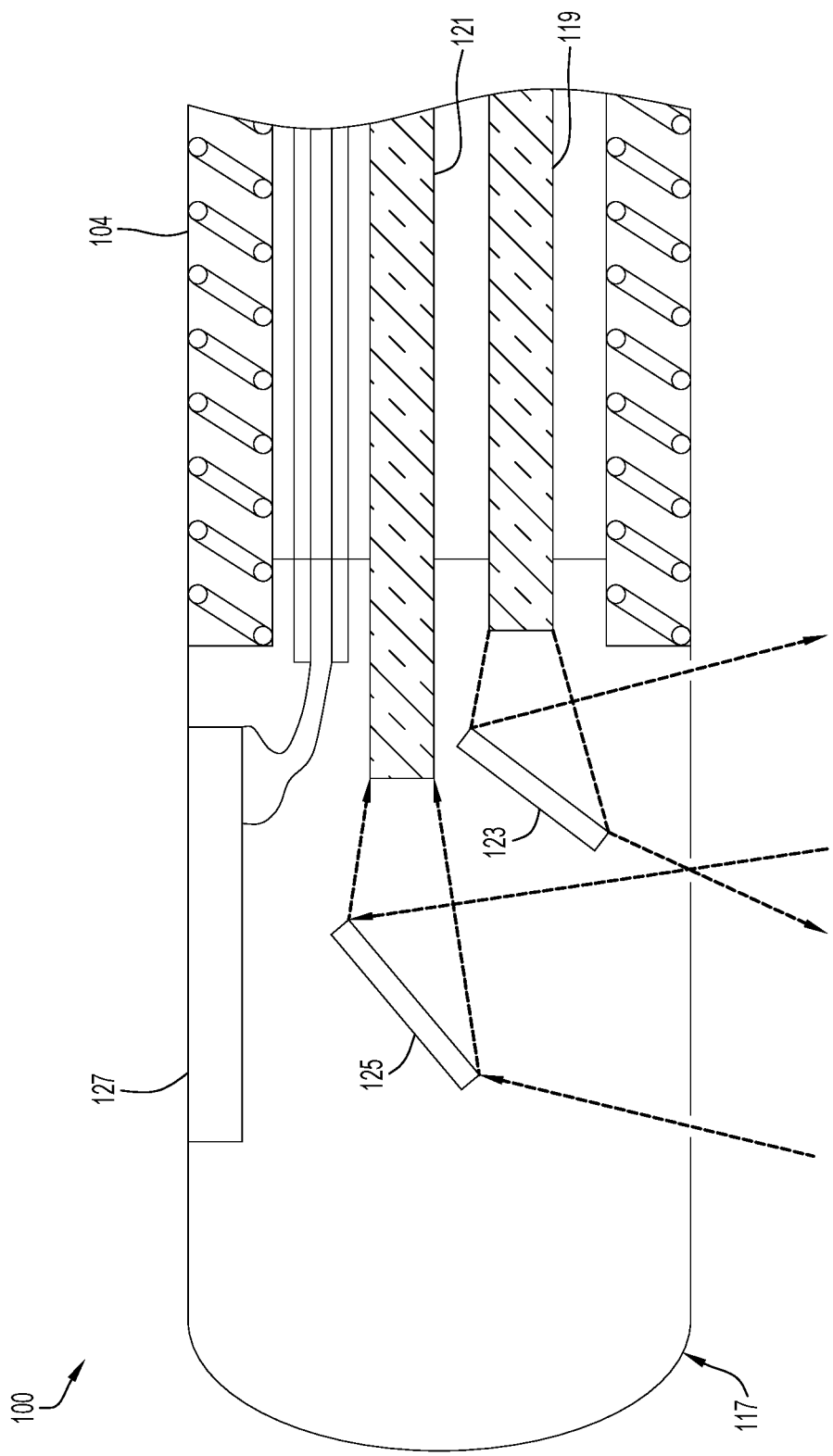
FIG. 3 is an enlarged view of the imaging tip at the distal end of the imaging catheter shown in FIG. 2.
Figure 4:
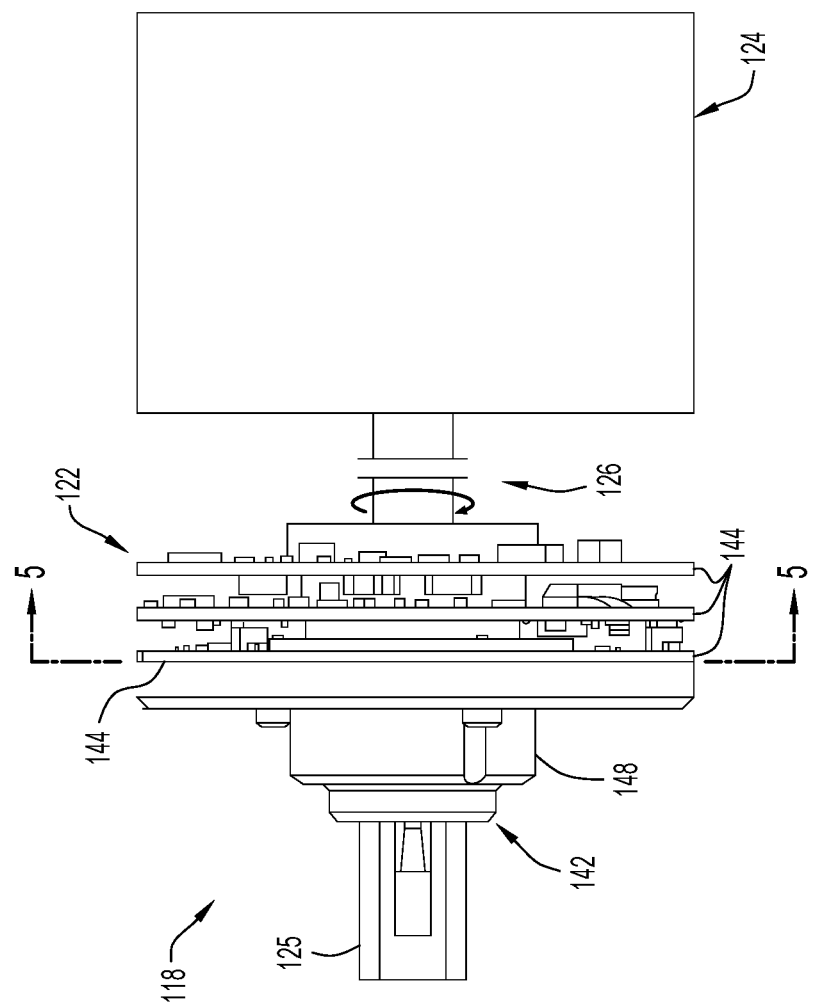
FIG. 4 is a side view of a rotor carriage assembly for pullback and rotation of an imaging tip in an imaging system according to an example embodiment of the present invention.

Referring now to FIGS. 2 and 3, it can be seen that the imaging catheter 100 includes an imaging tip 117 located at a distal end of the torque cable 104. The imaging tip 117 includes at least one imaging component selected from the group comprising an optical element and an ultrasonic transducer. In the example shown, the imaging tip 117 includes optical elements to perform NIRS imaging and an ultrasonic transducer 127 to perform IVUS imaging. The optical elements include a delivery optical fiber 119 and a collection optical fiber 121 that extend between proximal and distal ends of the torque cable 104. The distal ends of both the collection and delivery fibers are secured to the imaging tip 117 in alignment with other optical elements for guiding light to and from the optical fibers. To maintain proper alignment of the optical and/or ultrasonic components, the imaging tip 117 is preferably formed of a rigid material, such as a rigid plastic, metal, or ceramic material.

A near infrared light source such as a laser (see element 132 in FIG. 2) couples light into a proximal end of the delivery optical fiber 119 which guides the light distally to the reflective surface of a delivery mirror 123 located on imaging tip 117. Mirror 123 is positioned to redirect the delivered light toward the vessel wall via the outer sheath 102. A collection mirror 125, also disposed on the imaging tip 117, redirects light scattered from various depths of the vessel wall into the distal end of collection fiber 121 which transmits the collected light proximally in the catheter to an optical detector (not shown) for processing and analysis. Other light redirectors can be used in place of mirrors (e.g., prisms, bends in the optical fiber tips, etc.).

The optical detector that receives the collected light from collection fiber 121 produces an electrical signal that contains a spectral signature indicating the composition of the vessel wall and, in particular, whether the composition is consistent with the presence of lipids found in a vulnerable plaque. The spectral signature in the electrical signal can be analyzed using a spectrum analyzer (not shown) implemented in hardware, software, or a combination thereof.

The rotor carriage 118 includes a non-rotating portion 124 and a rotating portion or rotor 122 coupled with the non-rotating portion. Rotor 122 is configured to rotate about a longitudinal axis of the housing 115. For example, a motor may be disposed on the non-rotating portion 124 and the rotor 122 may be mounted on a rotating drive shaft of the motor that is aligned with a longitudinal axis of the housing 115. Rotor 122 includes a coupling 125 adjacent the distal opening 116 in the housing 115. The coupling 125 is configured to mate with the inner hub 108 of the imaging catheter 100 to cause the inner hub (and thus the torque cable 104) to rotate and translate linearly relative to the longitudinal axis of the outer sheath 102 in response to rotation and linear translation of the rotor 122 relative to the longitudinal axis of the housing 115. Coupling 125 and inner hub 108 include mating connectors for communicating optical and/or electrical signals between the rotor 122 and imaging components on the torque cable 104. Optical and/or electrical signals may be communicated between the rotor 122 and the non-rotating portion 124 via a slip ring 126 or other suitable rotary connector.

In an embodiment, one or more force or pressure sensors 128 may be located between the coupling 125 and another part of the rotor 122 to monitor compression of the torque cable 104, which is seen as an axial force applied to the rotor in a proximal direction along the axis of rotation the rotor (or a longitudinal axis of the housing). For example, the rotor 122 may include a printed circuit board (PCB) with a planar surface oriented perpendicular to the axis of rotation of the rotor 122, and the one or more sensors 128 may be mounted on a side of the PCB facing the coupling 125 (see, e.g., elements 128 in FIGS. 5 and 7). In an embodiment, the one or more sensors 128 may be superimposed with the coupling 125 (e.g., within a radius from the axis of rotation corresponding to a periphery of the coupling). The one or more sensors 128 may be disposed directly against the coupling 125, or an intermediate member may be disposed between the one or more sensors and the coupling. In an alternative embodiment, the one or more sensors may be incorporated into the inner hub 108 (e.g., by forming the hub in two or more pieces and positioning the one or more sensors between axially spaced pieces of the hub). Output(s) from the one or more sensors 128 (e.g., voltage across a sensor) indicative of an axial force applied to the rotor 122 by the torque cable 104 may be communicated to the controller 120 via the slip ring 126 and the non-rotating portion 124 of the rotor. Examples of suitable force sensors include, but are not limited to, piezoelectric sensors, resistive sensors, capacitive sensors, electromagnetic sensors, and optical sensors.

Console 114 includes a computer 130 for communicating with the controller 120 in the PBR and a laser 132 for providing a source of near infrared light for NIRS imaging. It will be appreciated that the pullback and rotation unit 112 and the console 114 may be combined into a single unit. Alternatively, if the pullback and rotation unit 112 and console 114 are separate, some or all of the functions of the controller 120 may be performed by the console and vice versa.

In operation, catheter 100 is attached to PBR 112 by mating inner hub 108 with coupling 125 on the rotor 122 and mating outer hub 106 with the distal opening 116 on the housing 115. After the system is powered on and initialized, the imaging tip 117 at the distal end of the torque cable 104 may be moved proximally and distally within the outer sheath 102 by moving the rotor 122 in the PBR 112 proximally and distally relative to the housing 115. If, while moving distally, the imaging tip 117 at the distal end of the torque cable 104 encounters a kink or other obstruction in the outer sheath 102 that prevents or inhibits further distal movement, the torque cable will compress and start to bunch up, creating a spring force that is translated back to the coupling 125 on the rotor 122. As a result, the coupling 125 is compressed against the force sensor(s) 128. An output from the force sensor(s) (e.g., a voltage or current) changes as they are compressed, signaling to the controller 120 in the PBR that something is wrong. In an embodiment, the controller 120 may be configured such that, once an output indicative of a force threshold is reached, the controller causes linear motion of the rotor carriage 118 in the distal direction to stop and the rotor carriage to "recoil" (a quick move or retraction in the proximal direction) to relieve the spring force in the system due to compression of the torque cable. The controller 120 may also be configured to inform the user (e.g., via a display on the PBR and/or the computer in the console) that there may be a kink in the catheter or some other force error condition preventing or inhibiting distal movement and that they should retract the outer sheath slightly in order to ease re-advancement of the inner core. Once the force error condition is resolved, the procedure may be resumed. In an example embodiment, the catheter 110 may be removed from the PBR after the procedure, and the PBR may be re-used with a different catheter for a new procedure.

Figure 5:
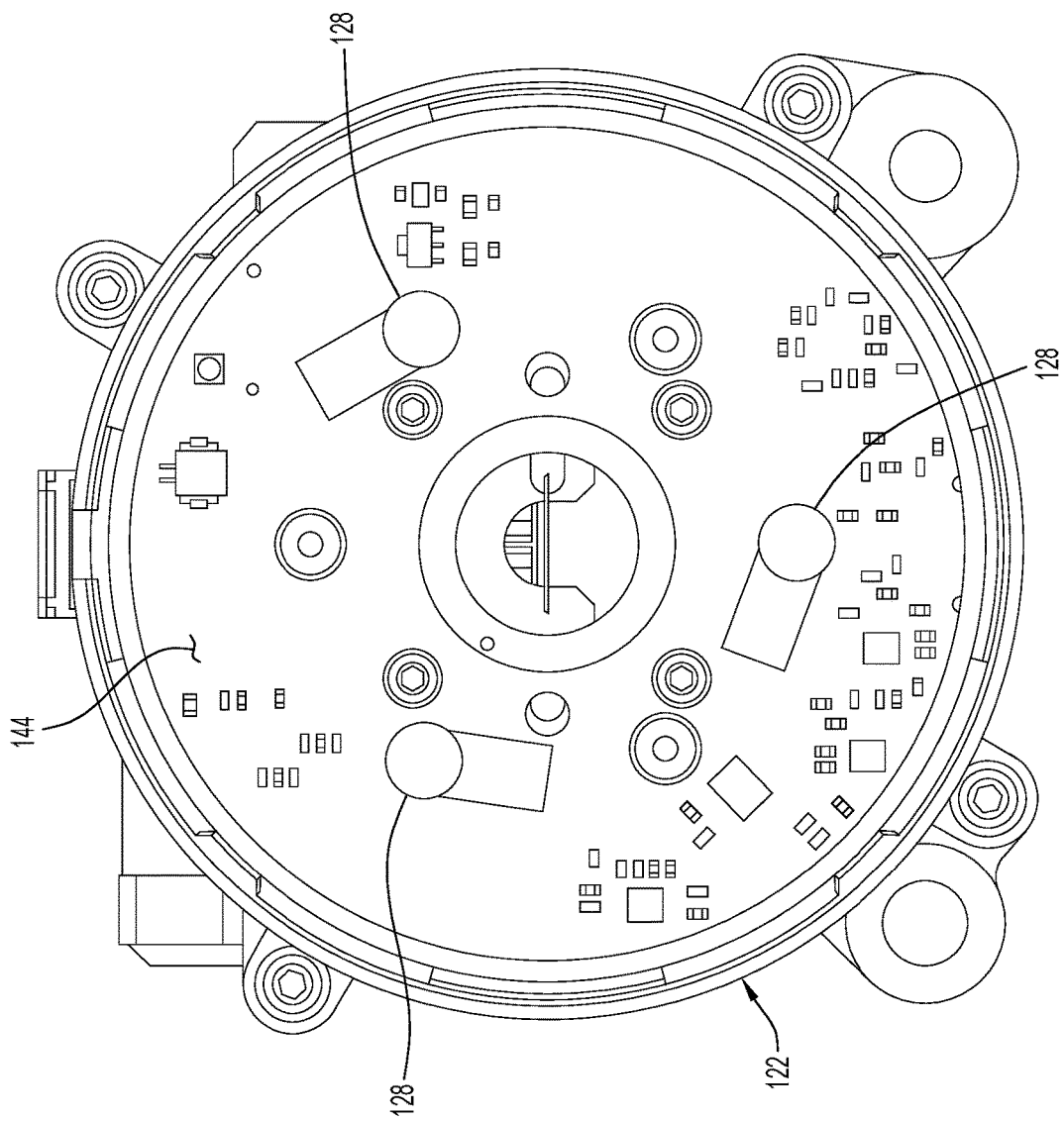
FIG. 5 is a sectional view of the rotor carriage assembly of FIG. 4, taken though line 5-5.
Figure 6:
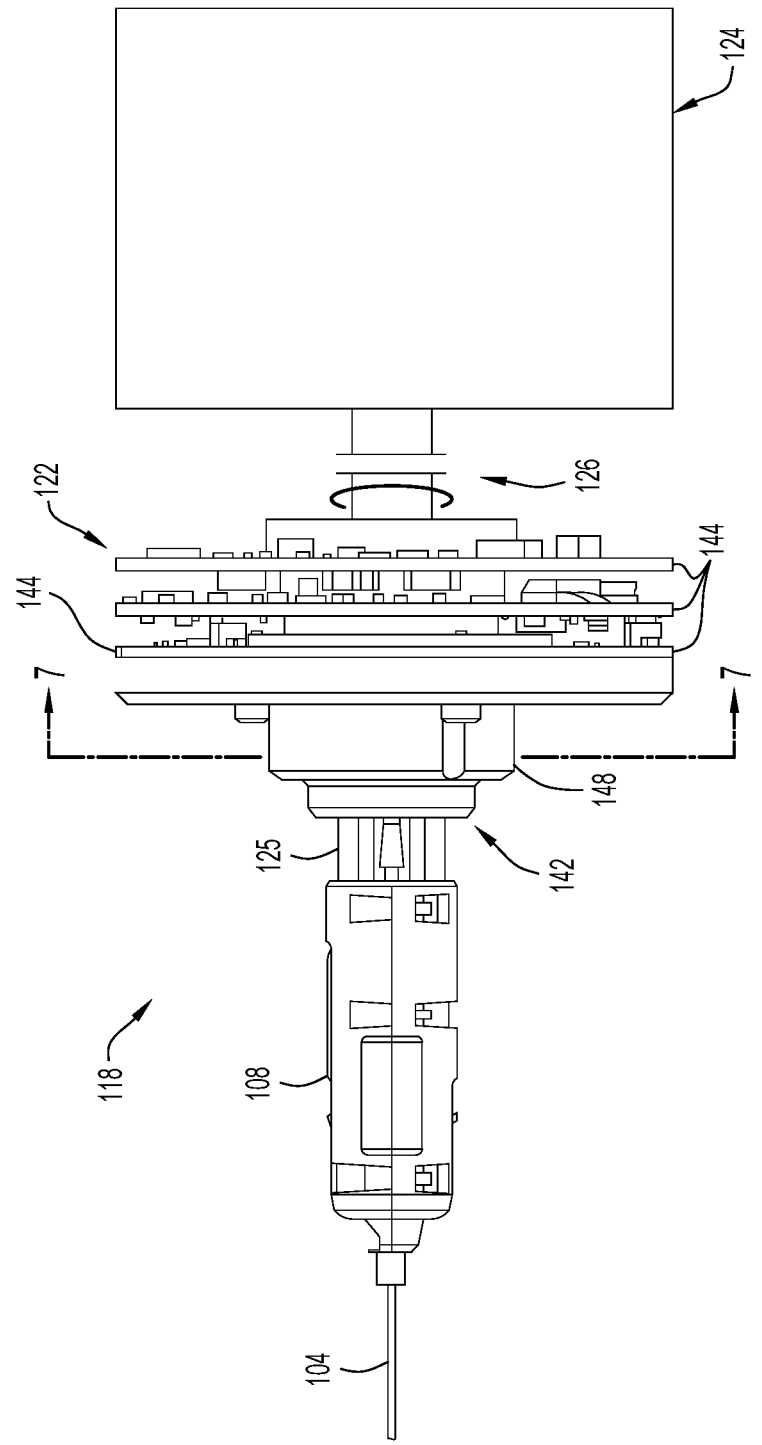
FIG. 6 is a side view of the rotor carriage assembly of FIG. 4 with an imaging catheter attached.

FIGS. 4-8 illustrate details of a rotor carriage 118 for pullback and rotation of an imaging tip according to an example embodiment. As noted above, the carriage 118 may be configured to be linearly translated in proximal and distal directions in a housing of a PBR. The rotor carriage 118 includes a non-rotating portion 124 and a rotating portion or rotor 122. A slip ring 126 is disposed between the rotating and non-rotating portions of rotor carriage 118 to facilitate transmission of optical and/or electrical signals therebetween. Rotor 122 is configured to rotate about a longitudinal axis of rotation and includes a nosepiece 142 at a distal end and a main body or frame mounting one or more PCBs 144 at a proximal end. The PCBs 144 are oriented perpendicular to the axis of rotation of the rotor and are stacked against the nosepiece 142. In the example embodiment shown, the PCB adjacent the nosepiece 142 is configured as a NIRS processing board, but it can be configured to have any desired function. As best seen in FIG. 5, three force sensors 128 are arranged on the distal side of the PCB facing the nosepiece 142. The force sensors 128 are disposed in a circular arrangement and are equiangularly spaced from one another (e.g., at about 120 degree intervals). Utilizing a plurality of sensors increases reliability of the force error detection system, and arranging the sensors at equiangular locations along a path of rotation may further increase reliability.

Figure 7:
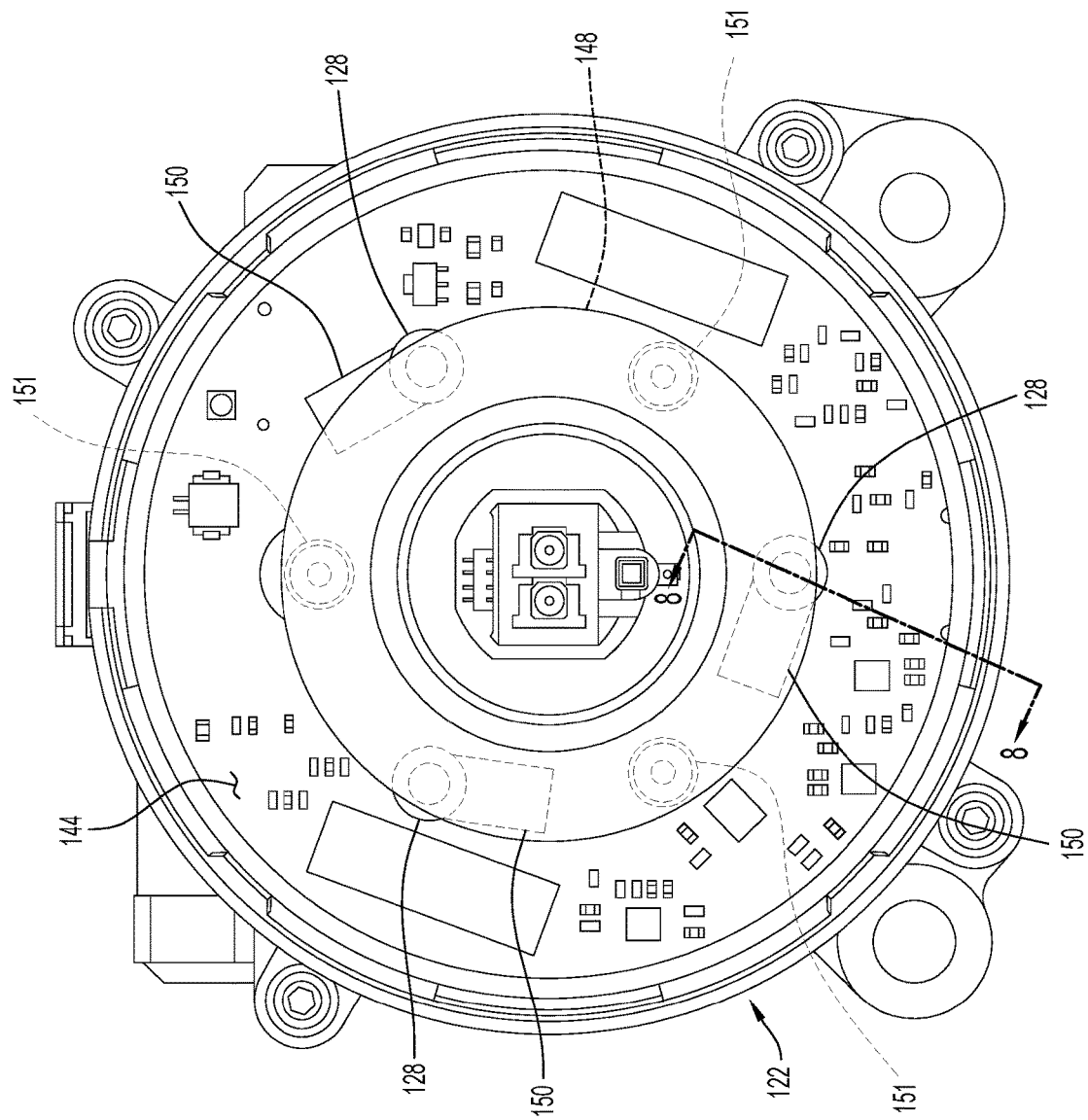
FIG. 7 is a sectional view of the rotor carriage assembly of FIG. 6, taken though line 7-7.
Figure 8:
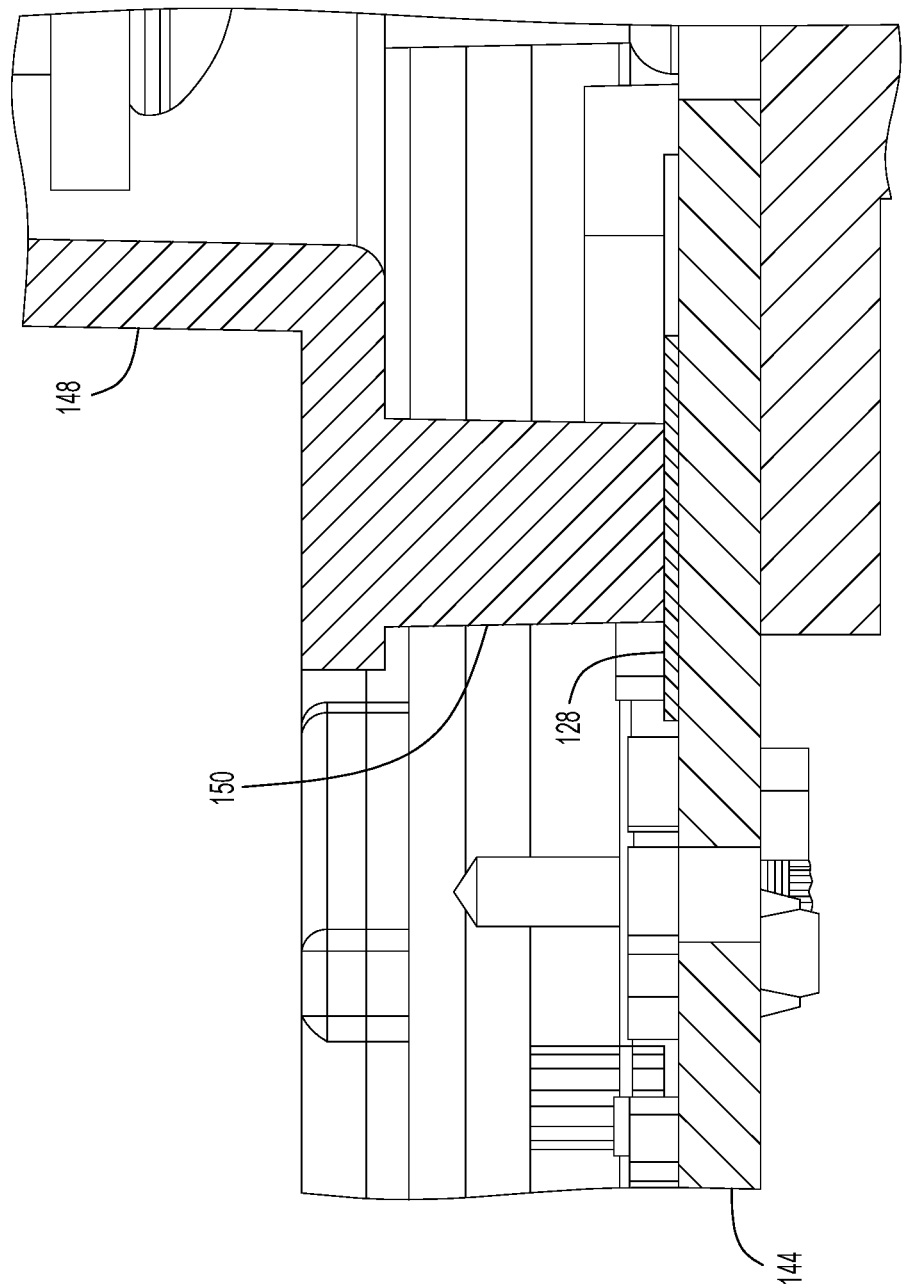
FIG. 8 is a partial sectional view of the rotor carriage assembly of FIG. 7, taken though line 8-8.

The nosepiece 142 includes a generally cylindrical collar 148 and a coupling 125 protruding distally from a center of the collar. As described above and shown in FIG. 6, the coupling 125 is configured to mate with an inner hub 108 at the proximal end of an imaging catheter. As best seen in FIG. 7, the sensors 128 are arranged to be superimposed with the collar 148 when viewed along the axis of rotation. That is, the sensors 128 are arranged along a circular path concentric with the collar 148 and having a radius about the same as or slightly smaller or larger than the collar. As best seen in FIG. 8, three legs 150 protrude proximally from the collar 148 towards the sensors 128. The nosepiece 142, including the coupling 125, the collar 148, and legs 150, is preferably formed of a rigid material, such as a rigid metal or plastic material, but can be formed of any suitable material capable of transmitting forces between the torque cable and the force sensors. In an example embodiment, the nosepiece 142 is configured to "float" (that is, move distally a small amount) relative to the rest of the rotor 122. For example, the nosepiece 142 may be mounted on the main body of the rotor 122 loosely (e.g., by installing fasteners 151 through the nosepiece into the main body of the rotor with a small axial gap (e.g., up to 0.5 mm) between a head of the fastener and the nosepiece). As a result, during operation, the legs 150 are free to move back and forth (i.e., proximally and distally) relative to the sensors 128 so that axial forces applied to the nosepiece by the torque cable are in turn applied to the sensors instead of the mounting. When an error condition occurs, such as when translating the torque cable 104 distally into a kinked portion of the outer sheath, the legs 150 are moved proximally against the force sensors 128. Alternatively, the legs 150 can be formed of an elastic material and maintained in contact with the force sensors, or elastic members (such as springs or flexible spacers) can be mounted between the nosepiece and the board mounting the force sensors or other part of the rotor.

Figure 9:
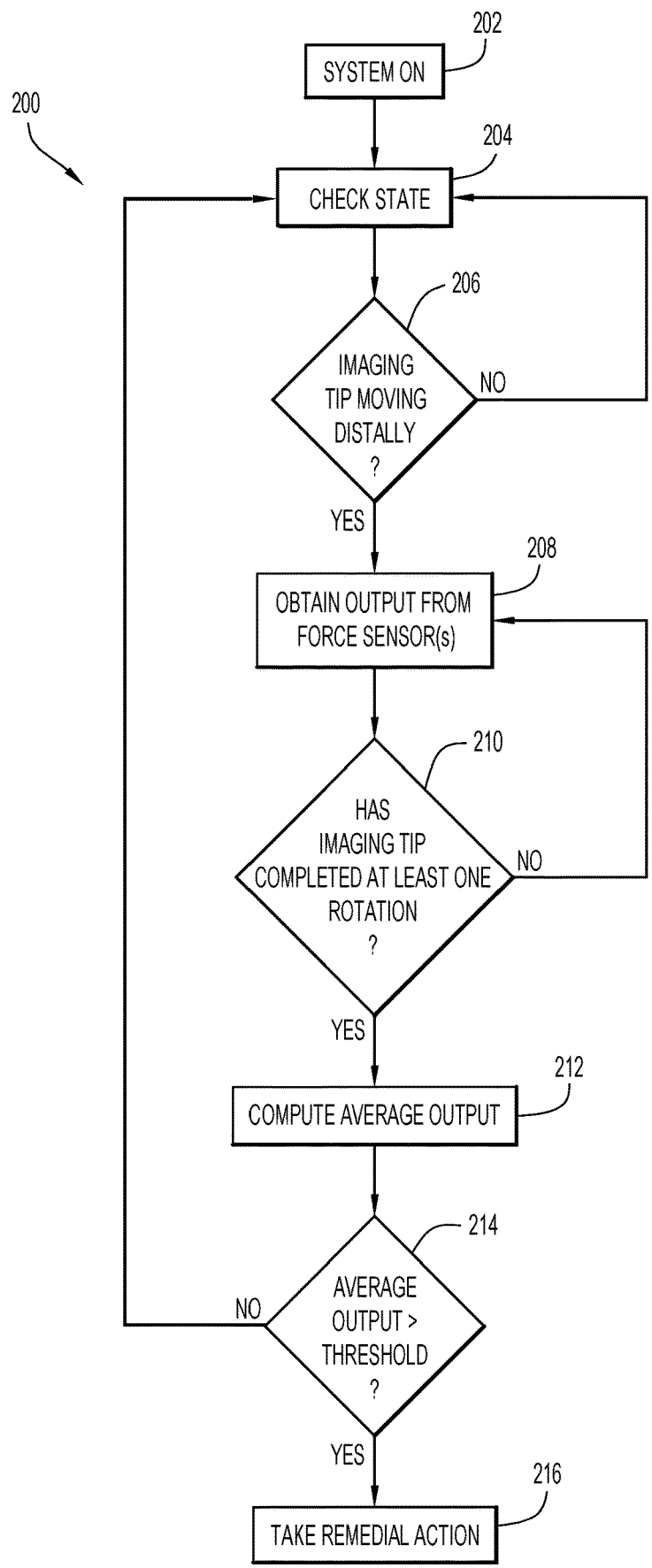
FIG. 9 is a flowchart illustrating a method of operating an imaging catheter system according to an example embodiment of the present invention.

FIG. 9 is a flowchart illustrating a method 200 of operating an imaging catheter system according to an example embodiment. The system is powered on at step 202. The system (e.g., via the controller) checks the state of the imaging tip at step 204 and determines whether the imaging tip is moving distally at step 206 (e.g., by checking whether a linear actuator is moving the rotor carriage distally). If the imaging tip is not moving distally, the method returns to step 204. If the imaging tip is moving distally, the system (e.g., via the controller) obtains output(s) from one or more force sensors positioned between the imaging tip and the PBR at step 208. The outputs may be analog signals (e.g., voltage across a sensor) or digital signals or any other type of electrical signals.

The system (e.g., via the controller) determines whether the imaging tip has completed a predetermined number of rotations greater than or equal to one at step 210 (e.g., by monitoring a rotary encoder in the PBR housing, or by monitoring rotational speed of the rotor and time). If the imaging tip has not completed the predetermined number of rotations, the method returns to step 208. If the imaging tip has completed the predetermined number of rotations, the system (e.g., via the controller) computes an average output at step 212. For example, if a single sensor is used, the system may compute an average of all outputs obtained from the single sensor over the predetermined number of rotations. Or, if multiple sensors are used, the system may compute an individual average for each sensor over the predetermined number of rotations and a combined average using the individual averages. In an example embodiment, the average is a rolling average, although other types of averaging or filtering can be used.

The system (e.g., via the controller) compares the average output to a predetermined threshold at step 214. In an example embodiment, the predetermined threshold may be set to correspond to a force indicative of a catheter malfunction. For example, the predetermined threshold may be set to correspond to a force indicative of the torque cable bunching up when the imaging tip encounters a kink or bend in the outer sheath that it cannot traverse. In such a case, the predetermined threshold may depend on the materials used for the catheter components and their configuration. Preferably, the predetermined threshold is set to correspond to a force below a level at which damage to the catheter components is likely to occur, so that remedial actions may be taken to relieve compression of the torque cable and continue use of the imaging catheter. In an example embodiment, the predetermined threshold may correspond to a force less than 10N. In another example embodiment, the predetermined threshold may correspond to a force in the range of 2N-6N.

If the average output is less than or equal to the predetermined threshold, the method returns to step 204. If the average exceeds the predetermined threshold, the system takes remedial action at step 216. For example, the system may automatically stop further linear translation of the imaging tip in the distal direction. The system may also automatically retract the imaging tip proximally a predetermined distance (e.g., 10 mm) to relieve compression of the torque cable. The system may stop rotation of the imaging tip or continue to rotate the imaging tip during retraction following a force error event. The system may also notify the user of the error condition (e.g., via a display on the PBR or via the computer in the console) so that the user may take remedial action (e.g., by retracting the outer sheath to eliminate the kink).

From the above, it will be appreciated that kinking of an outer sheath in an imaging catheter system and other force error conditions preventing or inhibiting distal translation of an imaging tip in the outer sheath can be addressed by mounting pressure or force sensors at various locations between the imaging tip and a PBR. A controller in the system may be configured to monitor an axial force exerted on the sensors in a proximal direction and to enter a force error state or mode when the imaging tip is moving distally in the sheath and the axial force measured by the sensors exceeds a predetermined threshold (e.g., suggesting that the linearly translating imaging tip is encountering a kink in the outer sheath or some other error condition preventing further linear translation). Since excessive force can indicate a dangerous condition, in the force error mode, the controller may be configured to cause one or more remedial actions to be performed.

While an example embodiment is shown in which three force sensors are spaced 120° apart on a NIR board in the PBR, it will be appreciated that other arrangements can be utilized. For example, fewer than three sensors or more than three force sensors may be utilized, although a plurality of sensors are preferred for greater reliability. If a plurality of sensors are used, they may be arranged in a uniform (e.g., equiangularly spaced) pattern or a non-uniform pattern. Also, the one or more force sensors may be positioned at various locations in the imaging catheter system, such as between the imaging tip and the torque cable, between the torque cable and the inner hub, between axially spaced portions of the inner hub, between the inner hub and the rotor coupling, and between parts of the rotor.

Furthermore, while an example embodiment is described in which the output used for force detection is an average output over a period of time, it will be appreciated that other algorithms may be used. For example, the output used for force detection may be an average output over a period of time as described above, or a sum of outputs over a period of time, or a maximum output over a period of time, or a median output over a period of time, or an output derived from fewer than all of the sensors (e.g., the highest two out of three, etc.), or an output that excludes outliers, or a combination of the foregoing.

In addition, while an imaging tip having optical and/or ultrasonic components is described, it will be appreciated that the imaging tip can include components for performing therapy, such as tissue ablation, in addition to or in lieu of imaging components.

As noted above, the predetermined threshold may correspond to a force indicative of a kink or other obstruction or condition of the catheter that prevents or inhibits distal movement of the tip relative to the sheath. For example, the predetermined threshold may correspond to a force greater than an average axial force applied to the coupling during normal operation of the catheter. In a preferred embodiment, the predetermined threshold is below a level at which damage to the catheter components or other parts of the system will occur.

The above-described embodiments are provided by way of example and are not intended to limit the scope of the invention. Persons of ordinary skill in the art will appreciate that various modifications and changes may be made without departing from the spirit and scope of the invention. It should be understood that features described with respect to one embodiment may be used with other embodiments.

The invention claimed is:

1. A pullback and rotation unit for axially translating and rotating a torque cable in an elongate outer sheath of a catheter, the pullback and rotation unit comprising:
    a housing with a longitudinal axis;
    a rotor disposed in the housing and mounted to rotate and linearly translate relative to the longitudinal axis of the housing, the rotor further being configured to be coupled with a proximal end of the torque cable;
    a plurality of sensors configured on the rotor and radially spaced from an axis of rotation of the rotor and configured to provide an output indicative of an axial force exerted by the torque cable on the rotor;
    wherein the rotor includes a main body and a coupling mounted on the main body of the rotor, wherein the coupling is configured to couple with the proximal end of the torque cable, and wherein each of the plurality of sensors is mounted between the coupling and the main body of the rotor;
    wherein the coupling is mounted to be movable longitudinally relative to the main body of the rotor
    wherein the output is an average of an output from each of the plurality of sensors over a period of time for at least one full rotation of an imaging tip located at a distal end of the torque cable;
    a controller configured to, when the output exceeds a predetermined threshold, cause the rotor to automatically perform a remedial action to relieve at least a portion of the axial force, wherein the controller is configured to cause the rotor, when performing the remedial action, to retract proximally a predetermined distance; and wherein the predetermined threshold is set below a level at which damage to the outer sheath will occur due to a distal end of the torque cable being unable to traverse a portion of the outer sheath.

2. The pullback and rotation unit of claim 1, wherein each of the plurality of sensors is mounted on the main body of the rotor.

3. The pullback and rotation unit of claim 1, wherein the plurality of sensors includes at least three sensors.

4. The pullback and rotation unit of claim 3, wherein the at least three sensors are radially spaced equiangularly about the axis of rotation of the rotor.

5. The pullback and rotation unit of claim 1, wherein the predetermined threshold is set below 10N.

6. The pullback and rotation unit of claim 1, wherein the predetermined threshold is between 2N and 6N.

7. The pullback and rotation unit of claim 1, wherein the predetermined distance is sufficient to relieve at least the portion of the axial force applied to the rotor by the torque cable.

8. The pullback and rotation unit of claim 1, wherein the controller is configured to cause the rotor, when performing the remedial action, to continue rotating as it is retracted proximally the predetermined distance.

9. The method of claim 1, wherein the plurality of sensors are each configured to provide an output indicative of an axial force exerted by the torque cable on the rotor parallel to the axis of the rotation of the rotor.

10. An intravascular imaging catheter system comprising:
a pullback and rotation unit for axially translating and rotating a torque cable in an elongate outer sheath of a catheter, the pullback and rotation unit comprising:
a housing with a longitudinal axis;
a rotor disposed in the housing and mounted to rotate and linearly translate relative to the longitudinal axis of the housing, the rotor further being configured to be coupled with a proximal end of the torque cable;
a plurality of sensors configured on the rotor and radially spaced from an axis of rotation of the rotor and configured to provide an output indicative of an axial force exerted by the torque cable on the rotor;
wherein the output is an average of an output from each of the plurality of sensors over a period of time for at least one full rotation of an imaging tip located at a distal end of the torque cable;
a controller configured to, when the output exceeds a predetermined threshold, cause the rotor to automatically perform a remedial action to relieve at least a portion of the axial force, wherein the controller is configured to cause the rotor, when performing the remedial action, to retract proximally a predetermined distance; and
wherein the predetermined threshold is set below a level at which damage to the outer sheath will occur due to a distal end of the torque cable being unable to traverse a portion of the outer sheath; and
an imaging catheter including an elongate outer sheath having a proximal end coupled with the housing, the torque cable being disposed in the outer sheath and having a proximal end coupled with the rotor, and an imaging tip located at a distal end of the torque cable and including at least one imaging component selected from the group consisting of an optical element and an ultrasonic transducer.

11. The intravascular imaging catheter system of claim 10, wherein the plurality of sensors are each configured to provide an output indicative of an axial force exerted by the torque cable on the rotor parallel to the axis of the rotation of the rotor.

12. A method of imaging a vessel using an intravascular imaging catheter system, comprising:
a pullback and rotation unit for axially translating and rotating a torque cable in an elongate outer sheath of a catheter, wherein the pullback and rotation unit comprises:
a housing with a longitudinal axis;
a rotor disposed in the housing and mounted to rotate and linearly translate relative to the longitudinal axis of the housing, the rotor further being configured to be coupled with a proximal end of the torque cable;
a plurality of sensors configured on the rotor and radially spaced from an axis of rotation of the rotor and configured to provide an output indicative of an axial force exerted by the torque cable on the rotor;
wherein the output is an average of an output from each of the plurality of sensors over a period of time for at least one full rotation of an imaging tip located at a distal end of the torque cable;
a controller configured to, when the output exceeds a predetermined threshold, cause the rotor to automatically perform a remedial action to relieve at least a portion of the axial force, wherein the controller is configured to cause the rotor, when performing the remedial action, to retract proximally a predetermined distance; and
wherein the predetermined threshold is set below a level at which damage to the outer sheath will occur due to a distal end of the torque cable being unable to traverse a portion of the outer sheath; and
an imaging catheter including an elongate outer sheath having a proximal end coupled with the housing, the torque cable being disposed in the outer sheath and having a proximal end coupled with the rotor, and an imaging tip located at a distal end of the torque cable and including at least one imaging component selected from the group consisting of an optical element and an ultrasonic transducer;
the method comprising: coupling the proximal end of the elongate outer sheath with the housing of the pullback and rotation unit;
coupling the proximal end of the torque cable with the rotor disposed within the housing of the pullback and rotation unit;
inserting the catheter into the vessel;
linearly translating the imaging tip distally relative to the outer sheath by linearly translating the rotor distally in the housing of the pullback and rotation unit;
receiving an output from at least one sensor indicative of an axial force applied to the rotor by the torque cable; and
based on the output from the at least one sensor exceeding a predetermined threshold, causing the rotor to automatically perform a remedial action to relieve at least a portion of the axial force wherein causing the rotor, when performing the remedial action, to retract proximally a predetermined distance;
wherein the predetermined threshold is set below a level at which damage to the outer sheath will occur due to the distal end of the torque cable being unable to traverse a portion of the outer sheath.

13. The method of claim 12, wherein the predetermined distance is sufficient to relieve at least the portion of the axial force applied to the rotor by the torque cable.

14. The method of claim 12, wherein, when performing the remedial action, the rotor is caused to continue rotating as it is retracted proximally the predetermined distance.

15. The method of claim 12, wherein the predetermined threshold corresponds to a force greater than an average axial force applied to the rotor during normal operation of the catheter.

16. The method of claim 12, wherein the plurality of sensors are each configured to provide an output indicative of an axial force exerted by the torque cable on the rotor parallel to the axis of the rotation of the rotor.

* * * * *